US006457250B1

(12) United States Patent
Mingus et al.

(10) Patent No.: US 6,457,250 B1
(45) Date of Patent: Oct. 1, 2002

(54) APPARATUS FOR MEASURING CONFORMANCE OF MANUFACTURED FOOD PRODUCT

(75) Inventors: J. David Mingus, New Hope, MN (US); Curtis M. DeMulling, Minneapolis, MN (US); Kristine K. Downing, Minneapolis, MN (US); Victoria Spadaro, Golden Valley, MN (US); Edwin T. Ta, Minneapolis, MN (US)

(73) Assignee: The Pillsbury Company, Minneapolis, MN (US)

( * ) Notice: Subject to any disclaimer, the term of this patent is extended or adjusted under 35 U.S.C. 154(b) by 0 days.

(21) Appl. No.: 09/410,412

(22) Filed: Oct. 1, 1999

(51) Int. Cl.$^7$ ................................................. G01B 3/14
(52) U.S. Cl. ......................... 33/562; 33/545; 33/1 BB
(58) Field of Search ........................... 33/562, 563, 565, 33/571, 573, 1 BB, 1 B, 1 F, 1 V, 501.05, 524, 525, 679.1, 545, 546, 549, 551; 116/DIG. 41; D10/64, 70, 71, 61; 426/231, 87

(56) References Cited

U.S. PATENT DOCUMENTS

| | | | | |
|---|---|---|---|---|
| 1,032,594 A | * | 7/1912 | Ferguson et al. | 33/480 |
| 2,452,385 A | * | 10/1948 | Merckel | 116/DIG. 41 |
| 2,705,451 A | * | 4/1955 | Mueller | 116/DIG. 41 |
| 3,347,179 A | * | 10/1967 | Haidinyak | 33/1 F |
| 3,874,085 A | * | 4/1975 | Atkins | 33/524 |
| 4,075,769 A | * | 2/1978 | Young | 33/524 |
| 4,120,094 A | * | 10/1978 | Pfaelzer | 33/1 V |
| 4,165,565 A | * | 8/1979 | Cloutier et al. | 33/524 |
| 4,672,748 A | * | 6/1987 | Perazzolo | 33/11 |
| 5,063,684 A | * | 11/1991 | Winters | 33/645 |
| 5,065,518 A | * | 11/1991 | Herrera | 33/1 BB |
| 5,505,977 A | * | 4/1996 | Neumeister | 426/549 |
| 5,528,517 A | * | 6/1996 | Loken | 33/1 V |

FOREIGN PATENT DOCUMENTS

| | | |
|---|---|---|
| DE | 24 08 841 | 9/1975 |
| DE | 196 00 521 | 7/1996 |
| JP | 04 350540 | 12/1992 |
| JP | 04 359388 | 12/1992 |
| JP | 10 238785 | 9/1998 |
| SU | 994984 | 7/1983 |
| SU | 1 254 380 | 8/1986 |

OTHER PUBLICATIONS

"Baking and Organoleptic Quality of Composite Flour Bread with Winged Bean, Triticale and Wheat"—Bakers Digest, Dec. 1980; vol. 54, No. 6.
On–Line Combined Color and Height Sensor for Bakeries, McFarlene I, Food Processing Automation, 43 34–39 (8 ref.), 1995.
Texture Measurements on Finished Baked Goods, Bourne M C, Advances in Baking Technology, 134–151 (4 ref.), 1995.
Food Technology in New Zealand (Oct.), 2 (0 ref.) 1994.

* cited by examiner

Primary Examiner—Diego Gutierrez
Assistant Examiner—Mirellys Jagan
(74) Attorney, Agent, or Firm—Kagan Binder, PLLC

(57) ABSTRACT

A grading template for measuring food product attributes for quality control and compliance. The template supports scales for measuring product attributes and has application for measuring size, shape, color and cell structure for baked bread.

5 Claims, 11 Drawing Sheets

APPARATUS FOR MEASURING CONFORMANCE OF MANUFACTURED FOOD PRODUCT

BACKGROUND OF THE INVENTION

The present invention relates to a quality control apparatus for a manufactured food product. In particular, the present invention relates to an apparatus for grading the quality of a manufactured food product.

Food products such as baked goods are manufactured in large qualities and packaged for sale. Product consistency is important for consumer confidence and sale. For example, for a baked good such as bread, product size, shape, cell structure and color are product attributes which can vary depending upon manufacturing conditions. It is desirable to grade product attributes against product standards for quality control testing. Variations in test procedures for grading product attributes can provide inconsistent and unreliable results. Periodic product testing monitors continued product compliance. Complex testing procedures and processes which require many testing devices increases testing complexity and deters periodic compliance testing. The present invention addresses these and problems for measuring product conformance.

SUMMARY OF THE INVENTION

The present invention relates to a grading template for measuring food product attributes for quality control and compliance. The template supports scales for measuring product attributes and has application for measuring such attributes as size, shape, color and cell structure for baked bread. The template supports multiple scales to provide a single device for grading product conformance.

DETAILED DESCRIPTION OF THE ILLUSTRATIVE EMBODIMENTS

Figure 1:
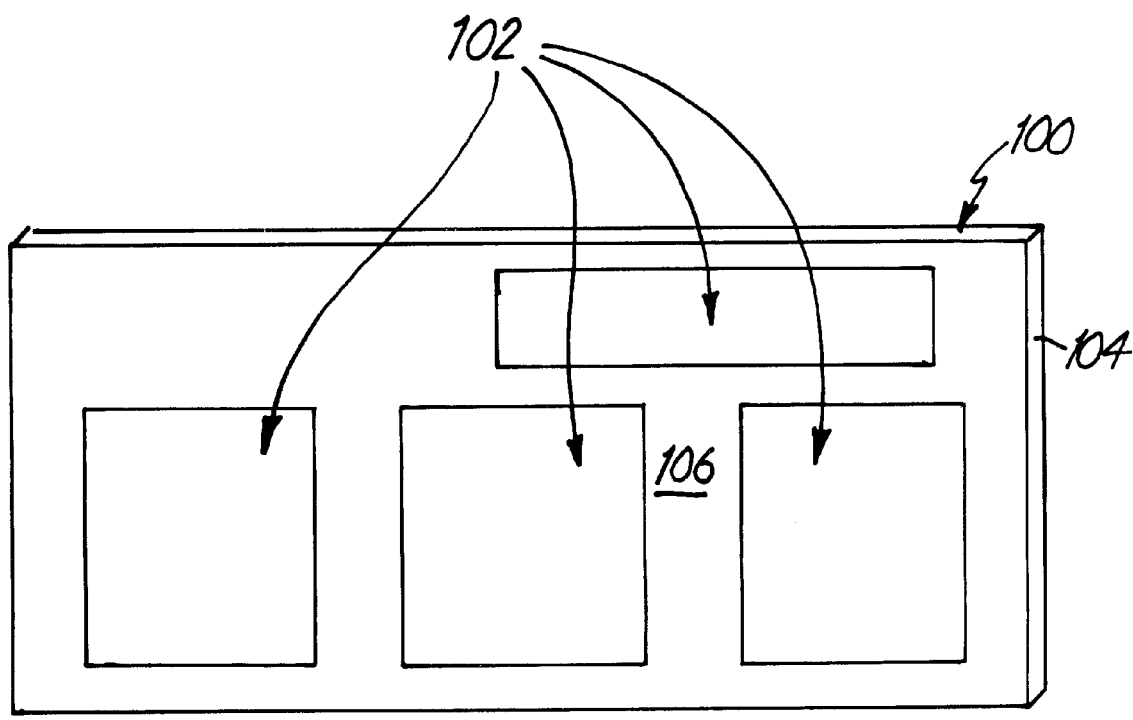
FIG. 1 is a perspective illustration of an embodiment of a template having a plurality of scales for grading a food product.

Attributes, such as size, shape, color and cell structure of baked goods influence consumer purchasing decisions and thus is desirable to measure product attributes for quality control and compliance. FIG. 1 illustrates an embodiment of a grading or scoring instrument for analyzing conformance of a food product for quality compliance. In the embodiment illustrated in FIG. 1, the apparatus includes a template 100 having a plurality of product compliance scales 102 supported on a template base 104. Scales 102 are used to measure food product compliance for quality control. Template base 104 includes a planar display surface 106 for scales 102 and can be a laminated paper material or formed of a plastic or other rigid base material of various shapes and sizes. The plurality of scales 102 supported on template 100 provides a single apparatus for measuring a plurality of product attributes for quality compliance.

FIGS. 2–6 illustrate an embodiment of a template 100 including scales 102-1, 102-2, 102-3, 102-4 for measuring product compliance for baked bread. As shown, scale 102-1 measures product dimensions; scale 102-2 measures shape; scale 102-3 measures color; and scale 104-4 measures cell structure. In the embodiment shown in FIGS. 2–3, product dimension scale 102-1 includes graduated measurement zones 110, 112, which are coded to identify variant or non-compliant product dimensions. As shown in detail in FIG. 3, scale 102-1 includes graduated measurement zones 110-1, 110-2, 110-3, 110-4, 110-5 and 112-1, 112-2, 112-3, 112-4, 112-5 for measuring product width (x) and height (y) dimensions. Product width and height dimensions are measured from reference positions 114, 116. In the embodiment illustrated in FIGS. 2–3 template 100 includes raised edge plates 118, 120 at an edge of scale 102-1 to define boundaries for reference positions 114, 116 for measurements.

Graduated measurement zones are spaced from reference positions 114, 116 to measure standard or compliant product dimensions and non-compliant product dimensions. In particular, in the embodiment shown, graduated measurement zones 110-3 and 112-3 are spaced from reference positions 114, 116 to measure a standard product dimension range. Graduated measurement zones 110-2, 110-4 and 112-2, 112-4 are spaced from reference positions 114, 116 to measure a marginal product dimension range. Graduated measurement zones 110-1, 110-5 and 112-1, 112-5 measure unacceptable product dimensions. Width and height product dimensions in zones 110-1, 112-1 are too small and width and height product dimensions in zones 110-5, 112-5 are too large or oversized. Additionally, numerical indicia can be included to measure product dimensions.

Dimension zones 110, 112 are coded to easily determine compliant and non-compliant product dimensions for grading product compliance results. In the embodiment shown, zones 110, 112 are color coded for ease of identification. Zones 110-3, 112-3 are colored green for acceptable width and height dimensions; zones 110-2, 110-4, 112-2, 112-4 are colored yellow for marginal compliance; and zones 110-1, 110-5 and 112-1, 112-5 are colored red for unacceptable product dimensions. Although a color coded scale is described for distinguishing compliant and non-compliant product dimensions, application is not limited to color coding and other indicia can be used for distinguishing measurement zones.

As shown, dimension scale 102-1 includes a thickness measurement scale 122 on edge plate 118 which extends above a base surface 124 of the template 100.

Base surface 124 defines a reference position for thickness measurements and scale 122 includes multiple measurement zones 126-1, 126-2, and 126-3 graduated from base surface 124 to measure product thickness compliance. Zone 126-2 is graduated to measure compliant thickness dimensions and zones 126-1 and 126-3 measure noncompliant thickness measurements. In zone 126-1 bread is too thin, and in zone 126-3 bread is too thick. Thus, as described, dimension scale 102-1 includes multiple measurement axis for width, height and thickness measurements using a single device. Although a particular number of gradations or zones are described for width, height and thickness measurements, application is not limited to the specific graduations and number shown.

Figure 2:
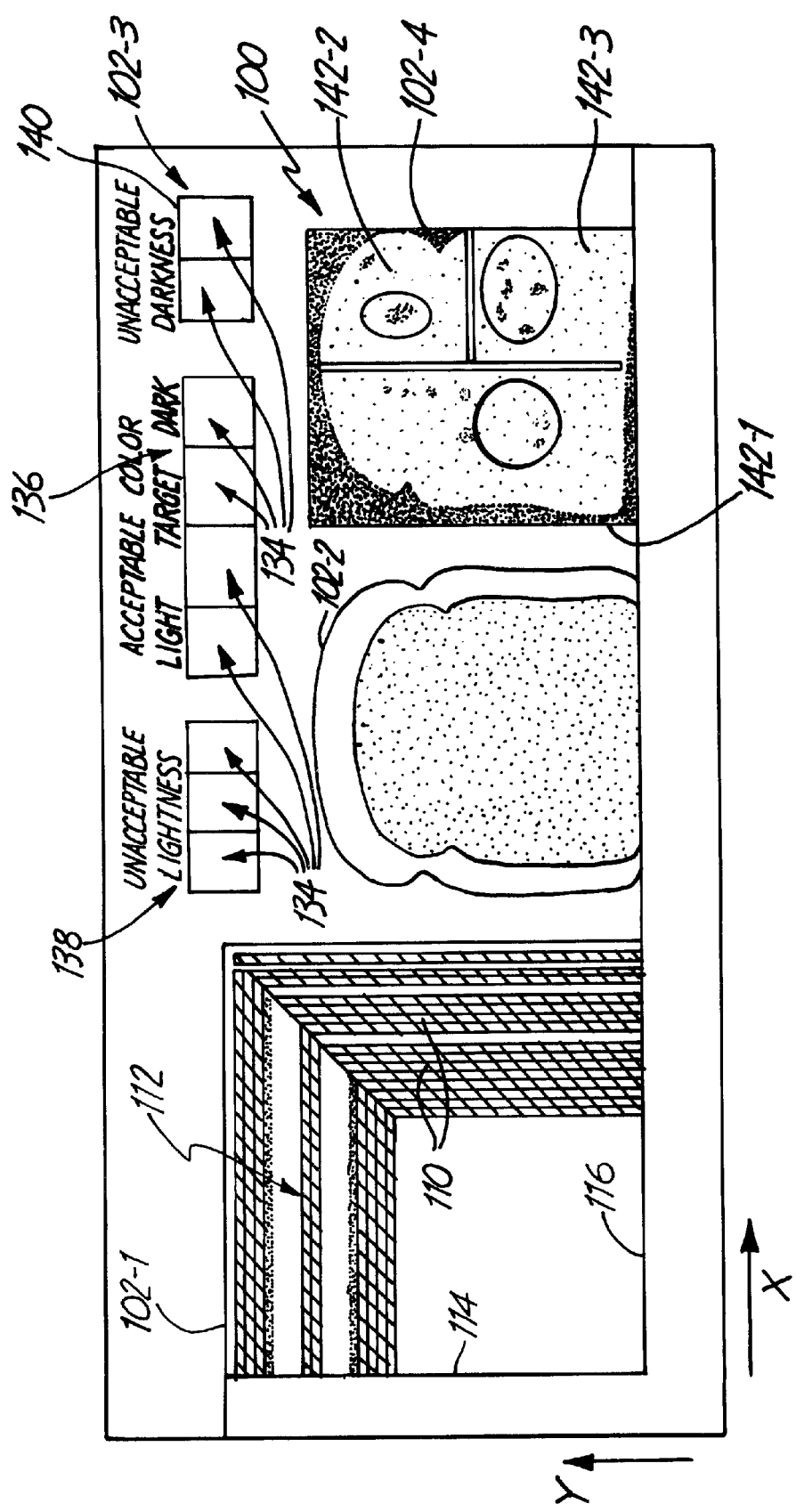
FIG. 2 is a plan view of a template having a plurality of scales for grading a bread product.
Figure 4:
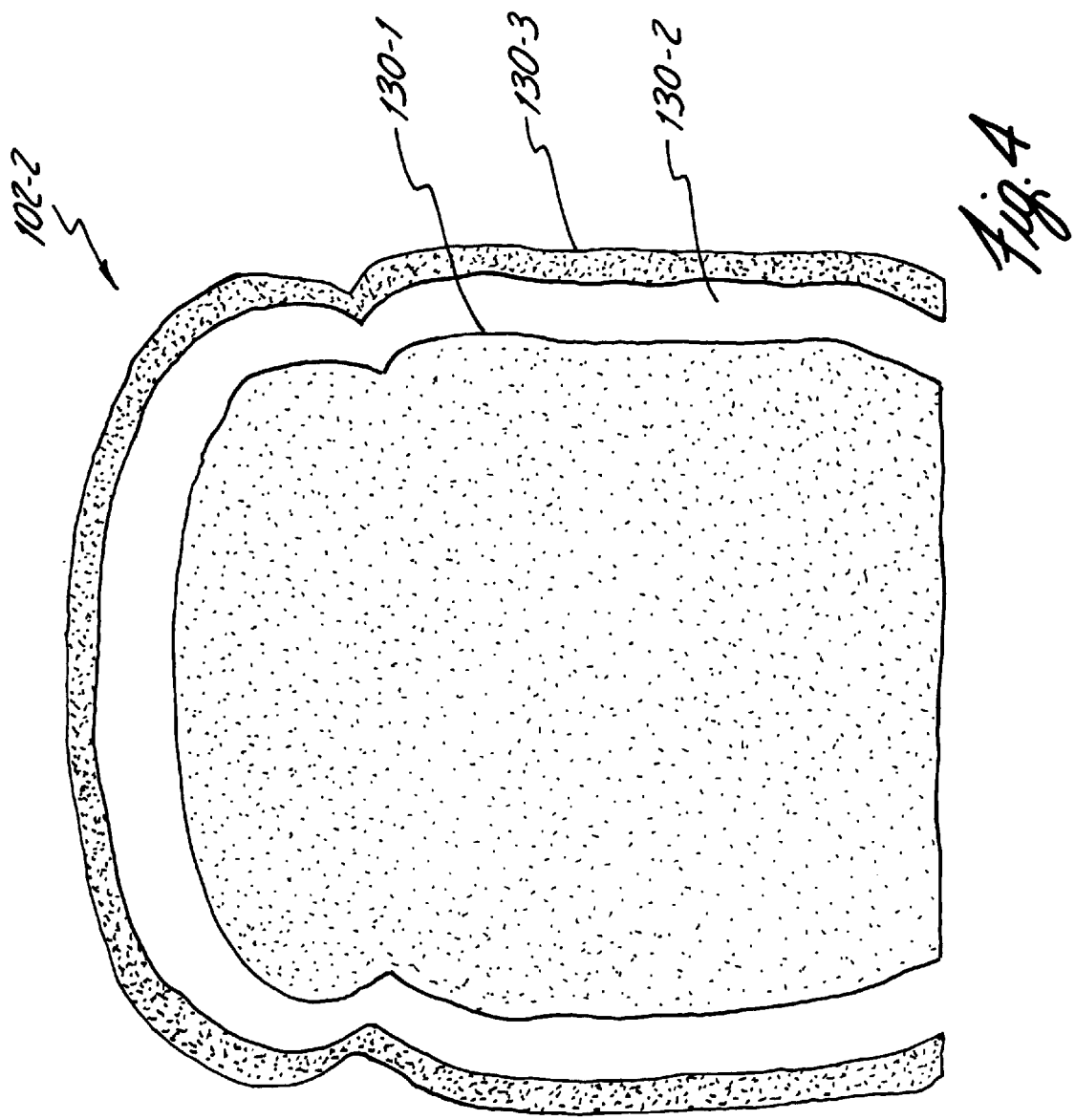
FIG. 4 is a plan view of an embodiment of a shape scale.

Template includes shape scale 102-2 as illustrated in FIGS. 2 and 4. Shape scale 102-2 includes graduated profile zones 130-1, 130-2, 130-3 to provide shape measurements. A bread product is placed on the scale to align with profile zone 130-1 to measure profile or shape compliance. If the contour of the bread extends beyond zone 130-1 into zone 130-2, product compliance is marginal and if product extends into zone 130-3 product shape is out of compliance. In the embodiment illustrated in FIG. 4, profile zone 130-1 is colored green for acceptable, zone 130-2 is colored yellow for marginal and zone 130-3 is colored red for out of range or unacceptable product shape. Although specific color coded compliance zones are described, other code designations or zones can be used to measure shape compliance.

Figure 5:
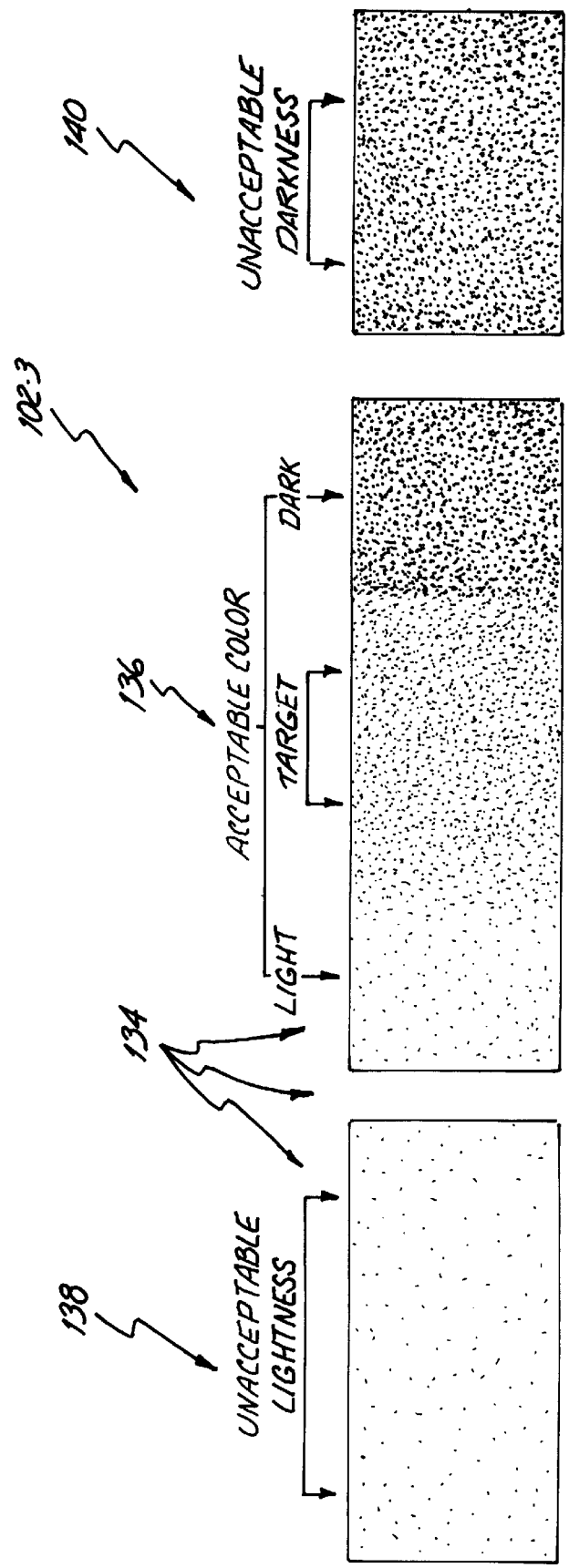
FIG. 5 is a plan view of an embodiment of a color scale.

Product color scale 102-3 illustrated in FIGS. 2 and 5 includes a plurality of color or shade samples 134 for measuring color compliance for baked bread. As shown, color scale 102-3 includes an acceptable or compliant color series or zones 136 and unacceptable series or zone 138, 140. Color series 136 includes samples 134 of an acceptable color range. Color series 138, 140 include color samples 134 outside the acceptable or compliant color range. In the embodiment shown, series 138 include color samples 134 which are too light and series 140 includes color samples 134 which are too dark in color. Color series 136, 138 and 140 are coded or labeled to distinguish compliant and non-compliant color samples or series.

Figure 6:
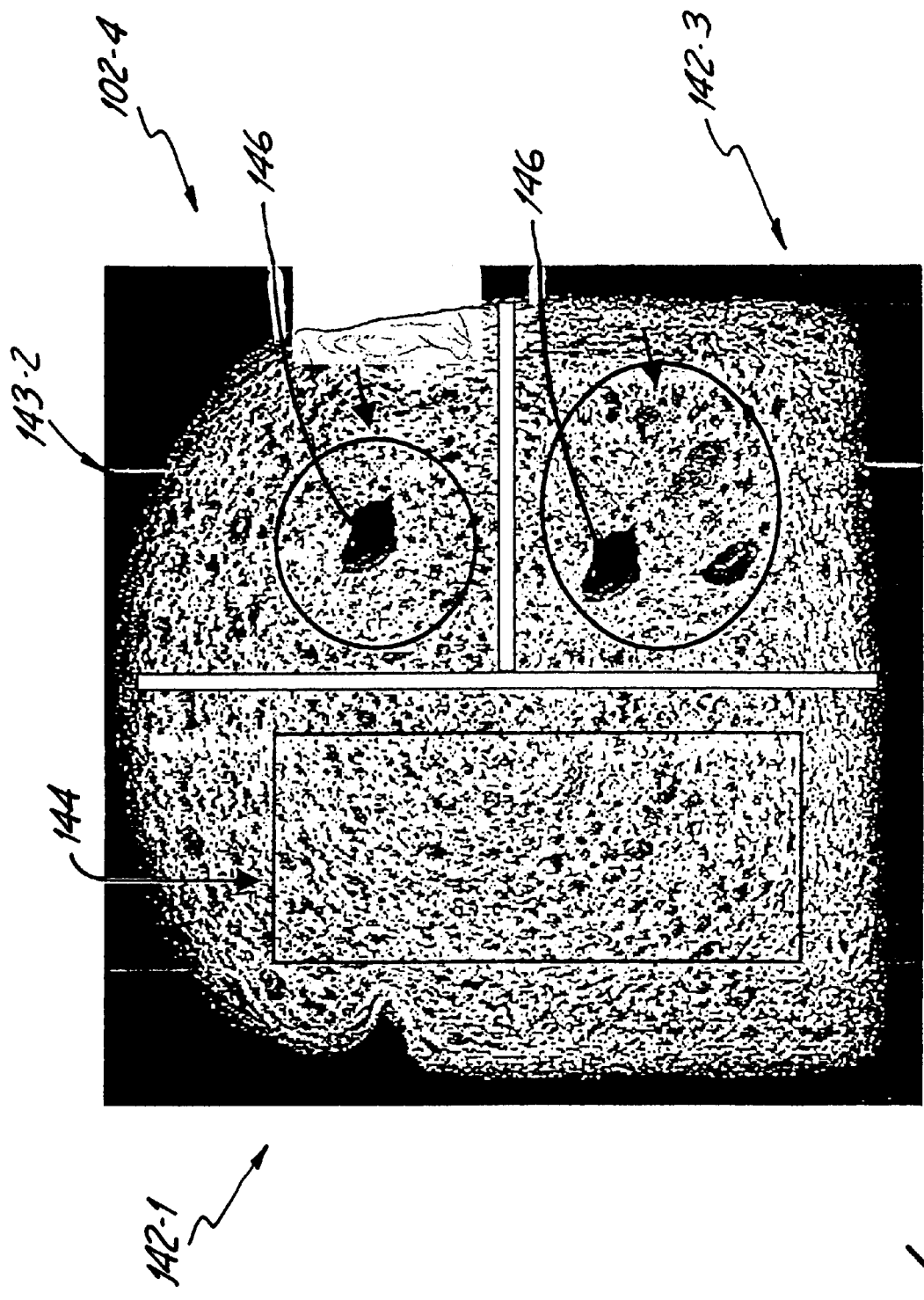
FIG. 6. is a plan view of an embodiment of a cell structure scale.

Cell structure scale 102-4 illustrated in FIGS. 2 and 6 includes cell structure samples 142-1, 142-2, 142-3 for measuring cell structure compliance. Sample 142-1 illustrates a conforming cell structure and samples 142-2, 142-3 illustrate a non-compliant or undesired cell structure. In particular, sample 142-1 illustrates a compliance hole structure and size 144 for a bread sample. As shown, samples 142-2, 142-3 illustrate non-compliant hole structures or size 146 for a bread sample. Test samples which have holes as large as or larger than holes 146 are unacceptable. Although particular compliant cell structure, size, shape, color and hole size are shown in FIGS. 2-6, application of the present invention is not limited to the specific product parameters or dimensions shown and parameters can vary as desired for a particular application. Although template 100 is illustrated for grading a bread product, application is not limited to bread products and can be used for grading such products as cakes, cupcakes, biscuits, muffins, rolls, baguettes, foccacia and the like.

Figure 7:
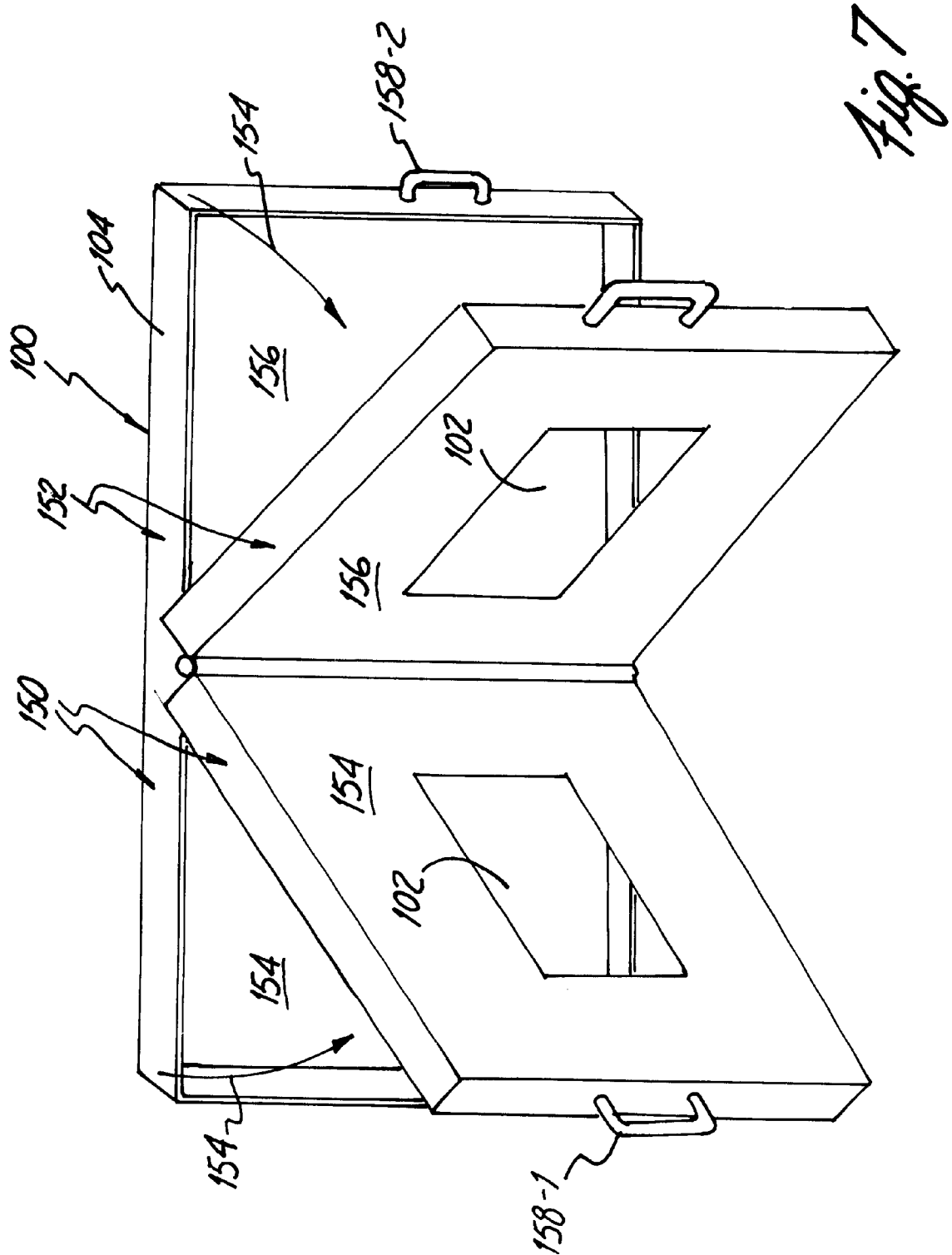
FIG. 7 is a perspective illustration of a collapsible template.

FIG. 7 illustrates a collapsible template base 104 having first and second template plates 150, 152 hingedly connected for collapsing the template as illustrated by arrow 154 for transport. In an example embodiment, template plates 150, 152 can be formed of a plastic material and a paper template is adhered to planar surfaces 154, 156 by a clear adhesive film or alternatively, template can be formed directly on the planar surfaces 154, 156 of the template base 104. Handles 158-1, 158-2 are attached to template plates 152, 154 to carry the template.

Figure 8:
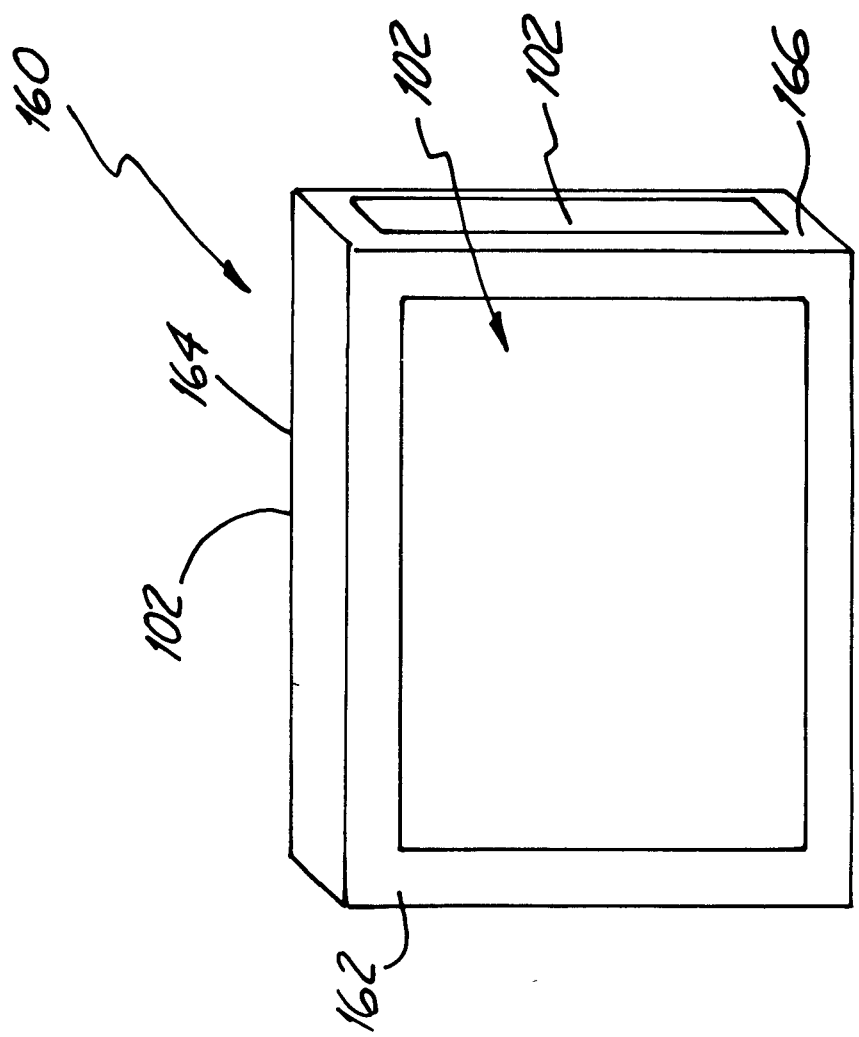
FIG. 8 is a perspective illustration of an alternate embodiment of a template.

FIG. 8 illustrates an alternate template 160 embodiment including a plurality of template surfaces displaying measurement scales 102. In the embodiment shown, front and back surfaces 162, 164 support scales, for example, front surface 162 supports a width and height dimension scale and back surface supports color and cell structure scales and an edge surface 166 supports a thickness scale.

Figure 3:
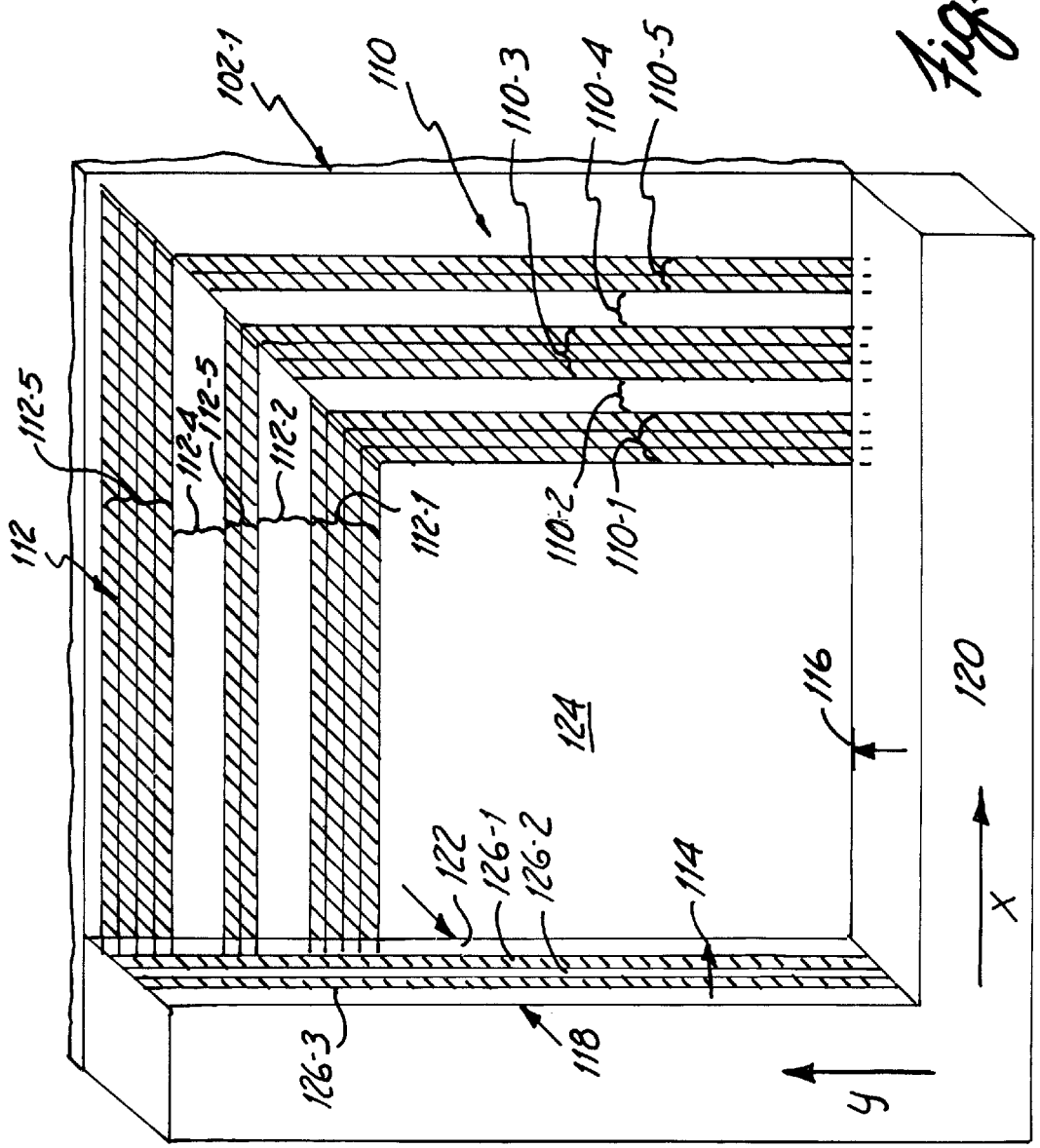
FIG. 3 is a perspective illustration of an embodiment of a dimension scale.
Figure 9:
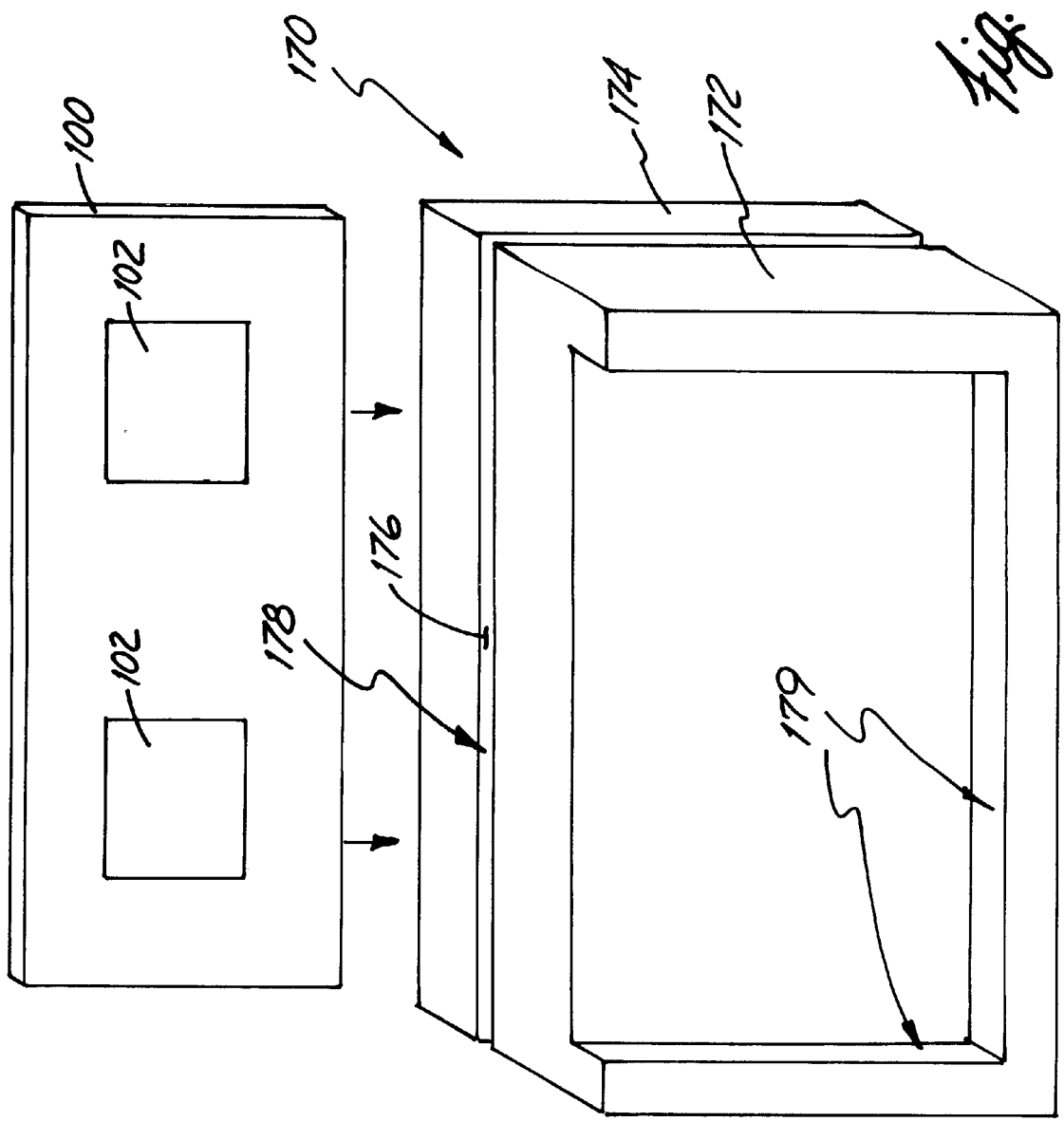
FIG. 9 is a perspective illustration of an embodiment of a template holder for supporting a template.

A flexible template can be supported for use in a template holder. FIG. 9 illustrates an embodiment of a template holder 170 which includes opposed plates 172, 174 connected in spaced relation to define a slot 176 therebetween. In the embodiment shown, template 100 is inserted into slot 176 through an opening 178. Plate 172 is formed of a clear or transparent material so that scale indicia are visible for use. Plate 172 includes perimeter ledge 179 surrounding scales 102 which forms edge plates to provide reference positions for dimension measurements as illustrated in FIGS. 2–3. Template 100 is inserted into slot 176 for use and can be removed and replaced to substitute different measurement scales for different products and applications. Alternatively, template 100 can be secured or fastened between plates 172, 174 for single application and use.

Figure 10:
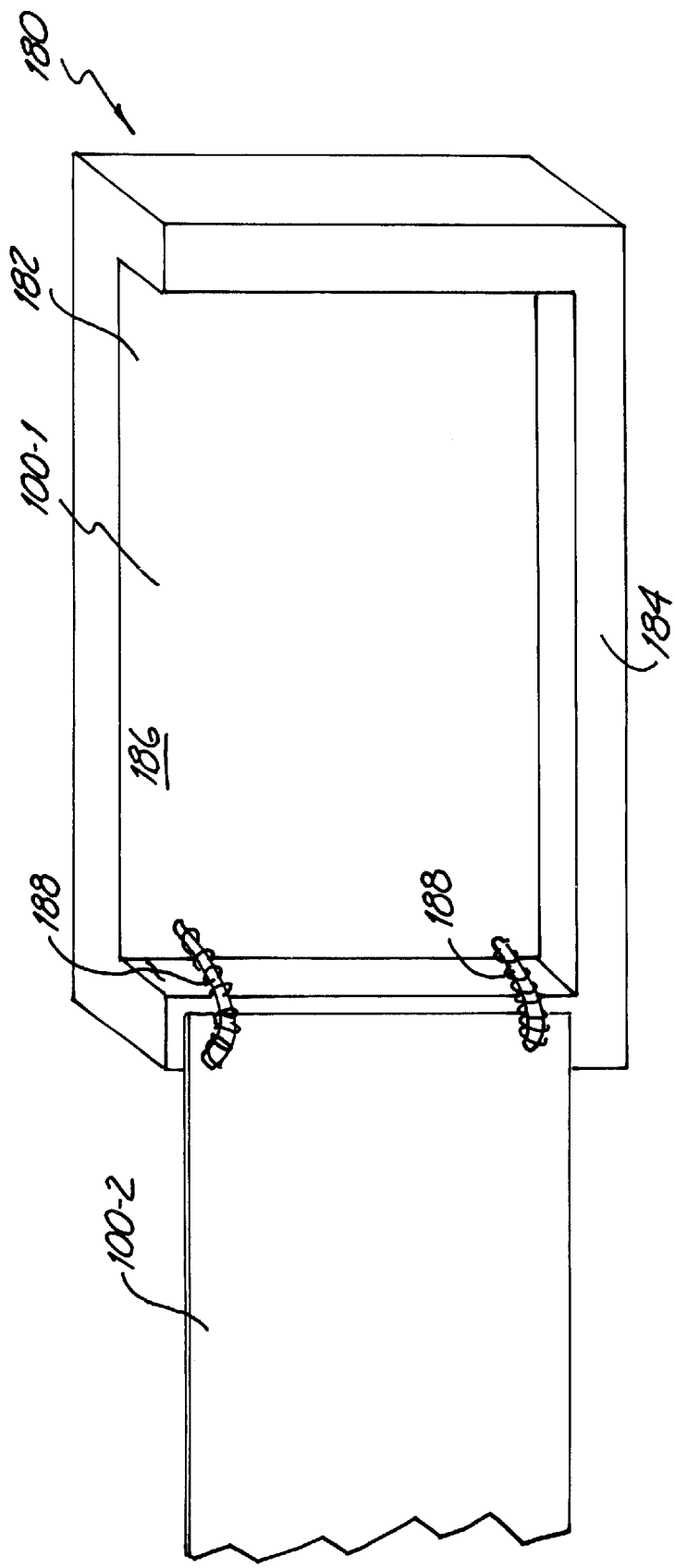
FIG. 10 is an alternate embodiment of a template holder for supporting a template.

FIG. 10 illustrates another embodiment of a template holer 180. As shown, holder 180 includes a base plate 182 including a perimeter ledge 184 surrounding a template cavity 186. Ledge 184 includes rings 188 for movable securing a plurality of templates 100-1, 102-2 for use. Templates are flipped into cavity 186 until the desired template is visible for use. Alternatively rings 188 support a plurality of template pages having a scale thereon which are bound by rings 188 to collectively form a template.

As shown, perimeter ledge 184 is located along the edge of a template supported in cavity 186 to define reference positions for dimension measurements as previously described. One end of the rings 188 is connected to a planar surface of cavity 186 and another is connected to ledge 184. Rings 188 extend through holes in templates to secure templates to holder 180 so that the template lays flat in the cavity 186. The flat template abuts perimeter ledge 184 to define reference positions for dimension measurements as previously explained.

Figure 11:
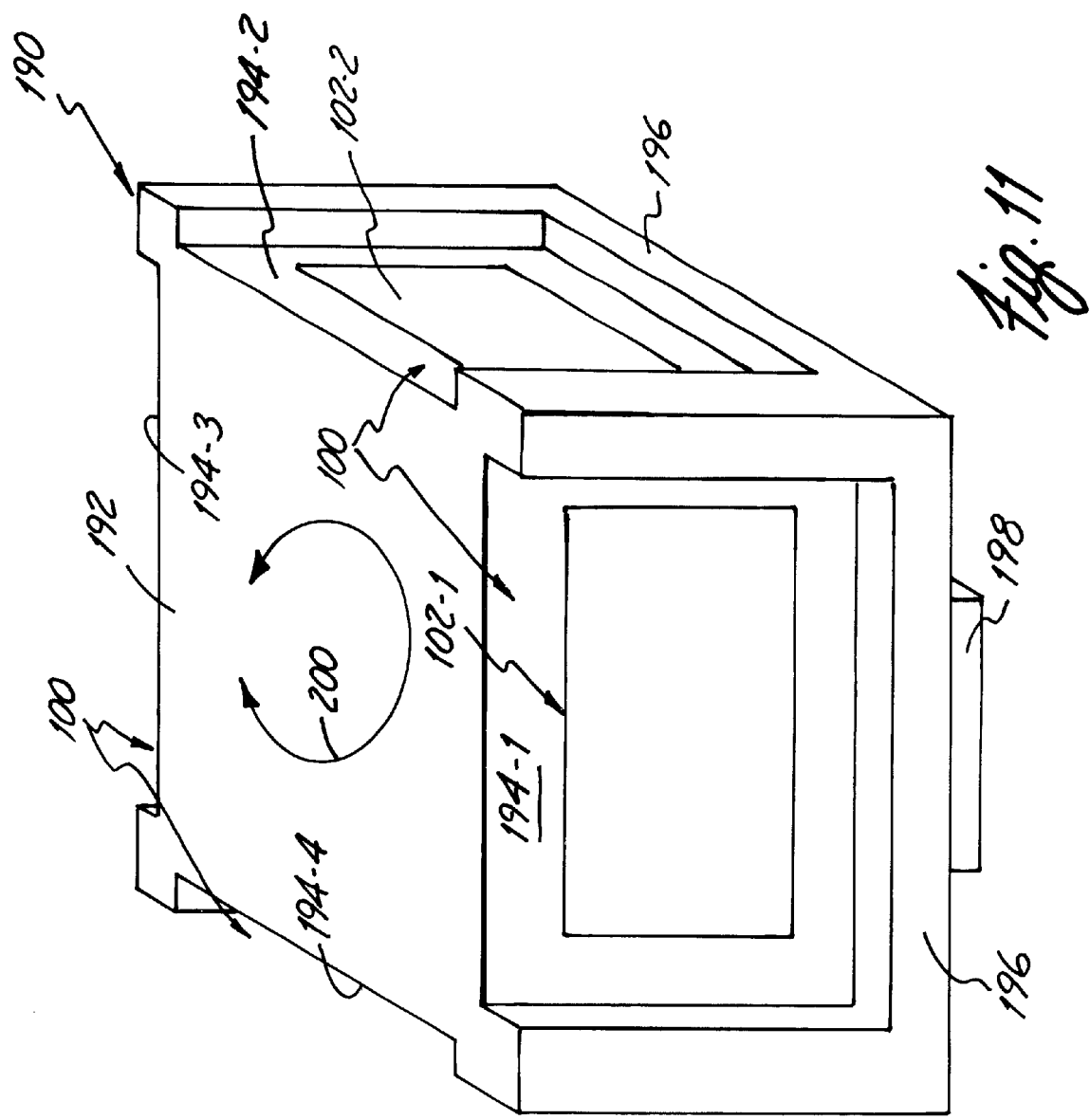
FIG. 11 is a perspective illustration of a template holder having a plurality of template surfaces.

FIG. 11 illustrates an embodiment of a three dimensional template holder 190. In the embodiment shown, holder 190 includes a template block 192 including a plurality of template surfaces 194-1, 194-2, 194-3, 194-4 which display a scale 102 and are surrounded by a perimeter ledge 196 to support a baked product, such as bread, for compliance measurement. Template surfaces are coupled to block to collectively form a template. Block 192 is rotationally coupled to base 198 to rotate as illustrated by arrow 200 for viewing multiple template surfaces 194-1, 194-2, 194-3, 194-4.

Although the present invention has been described with reference to preferred embodiments, workers skilled in the art will recognize that changes may be made in form and detail without departing from the spirit and scope of the invention.

What is claimed is:

1. A food product grading template apparatus comprising:
a template base; and
a template including a plurality of food product grading scales including at least one food product grading scale capable of measuring an aspect other than dimension, each food product grading scale directed to an independent aspect of conformance of the food product with food product acceptability indicia of conformance, at least one food product grading scale directed to aspect of conformance of the food product that is independent of size and at least one food product grading scale that includes multiple measurement axes for width, height and thickness measurements, whereby multiple independent aspects of conformance of a food product for quality acceptability can be measured.

2. The apparatus of claim 1 wherein at least one of the plurality of food product grading scales is a product shape scale.

3. The apparatus of claim 1 wherein at least one of the food product acceptability indicia of conformance comprises color.

4. The apparatus of claim 3 wherein the at least one food product acceptability indicia of conformance comprises a compliant measurement zone, a marginal measurement zone and a noncompliant measurement zone.

5. The apparatus of claim 4 wherein the compliant measurement zone is green, the marginal measurement zone is yellow and the non-compliant measurement zone is red.

* * * * *